(12) United States Patent
Mineo

(10) Patent No.: US 10,026,018 B2
(45) Date of Patent: Jul. 17, 2018

(54) MEDICAL IMAGE CLASSIFICATION SYSTEM, MEDICAL IMAGE CLASSIFICATION METHOD, AND MEDICAL IMAGE CLASSIFICATION APPARATUS

(71) Applicant: CASIO COMPUTER CO., LTD., Shibuya-ku, Tokyo (JP)

(72) Inventor: Shigeki Mineo, Hino (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 63 days.

(21) Appl. No.: 14/975,269

(22) Filed: Dec. 18, 2015

(65) Prior Publication Data

US 2016/0217347 A1 Jul. 28, 2016

(30) Foreign Application Priority Data

Jan. 28, 2015 (JP) .................................. 2015-014838

(51) Int. Cl.
*G06K 9/00* (2006.01)
*G06K 9/62* (2006.01)
(Continued)

(52) U.S. Cl.
CPC .......... *G06K 9/6267* (2013.01); *A61B 5/0013* (2013.01); *A61B 5/441* (2013.01);
(Continued)

(58) Field of Classification Search
CPC ..... A61B 5/0013; A61B 5/0077; A61B 5/441; A61B 5/444; G06F 19/321; G06K 9/6267
(Continued)

(56) References Cited

U.S. PATENT DOCUMENTS 8,798,367 B2 * 8/2014 Ellis .................... G06F 19/3462
382/117
2008/0275315 A1 11/2008 Oka et al.

FOREIGN PATENT DOCUMENTS

JP 2002271672 A 9/2002
JP 2005192944 A 7/2005
(Continued)

OTHER PUBLICATIONS

Japanese Office Action dated Apr. 24, 2018 issued in counterpart Japanese Application No. 2015-014838.

*Primary Examiner* — Manuchehr Rahmjoo
(74) *Attorney, Agent, or Firm* — Holtz, Holtz & Volek PC

(57) ABSTRACT

A medical image classification system includes an acceptance apparatus, a medical image acquisition apparatus, and a medical image classification apparatus. The acceptance apparatus includes an acceptor that accepts the input of patient identification information and medium identification information, and a first storage that stores first association information. The medical image acquisition apparatus includes an identification information acquirer, an image acquirer that acquires a medical image for diagnosing a patient, and a second storage that stores second association information. The medical image classification apparatus includes a first acquirer that acquires the first association information stored by the first storage, a second acquirer that acquires the second association information stored by the second storage, and a classifier that performs classification of the medical image identification information per the patient identification information based on the medium identification information in the first association information and the second association information.

9 Claims, 10 Drawing Sheets

(51) Int. Cl.
*G06F 19/00* (2018.01)
*A61B 5/00* (2006.01)
(52) U.S. Cl.
CPC ............ *A61B 5/444* (2013.01); *G06F 19/321* (2013.01); *A61B 5/0077* (2013.01)
(58) Field of Classification Search
USPC ....................................................... 382/128
See application file for complete search history.

(56) References Cited

FOREIGN PATENT DOCUMENTS

| | | | |
|---|---|---|---|
| JP | 2005278864 A | 10/2005 | |
| WO | 2007052502 A1 | 5/2007 | |

* cited by examiner

FIG. 5

```
ACCEPTANCE PROCESS
         ↓
S11  ACCEPT INPUTS OF
     PATIENT ID, BEACON ID, AND
     LENDING TIME
         ↓
S12  IS INPUT OF RETURN TIME  ──No──┐
     ACCEPTED?                       │
         ↓ Yes                       │
S13  CALCULATE USAGE TIME PERIOD     │
     FROM LENDING TIME               │
     AND RETURN TIME                 │
         ↓                           │
S14  STORE PATIENT ID, BEACON ID, AND│
     USAGE TIME PERIOD ASSOCIATED WITH
     EACH OTHER
         ↓
        END
```

FIG. 6

PATIENT SPECIFICATION TABLE

| PATIENT ID | BEACON ID | USAGE TIME PERIODS OF BEACON |
|---|---|---|
| A | 1 | 9:00 ~ 10:00 |
| B | 2 | 9:30 ~ 10:30 |
| C | 1 | 10:05 ~ 10:30 |

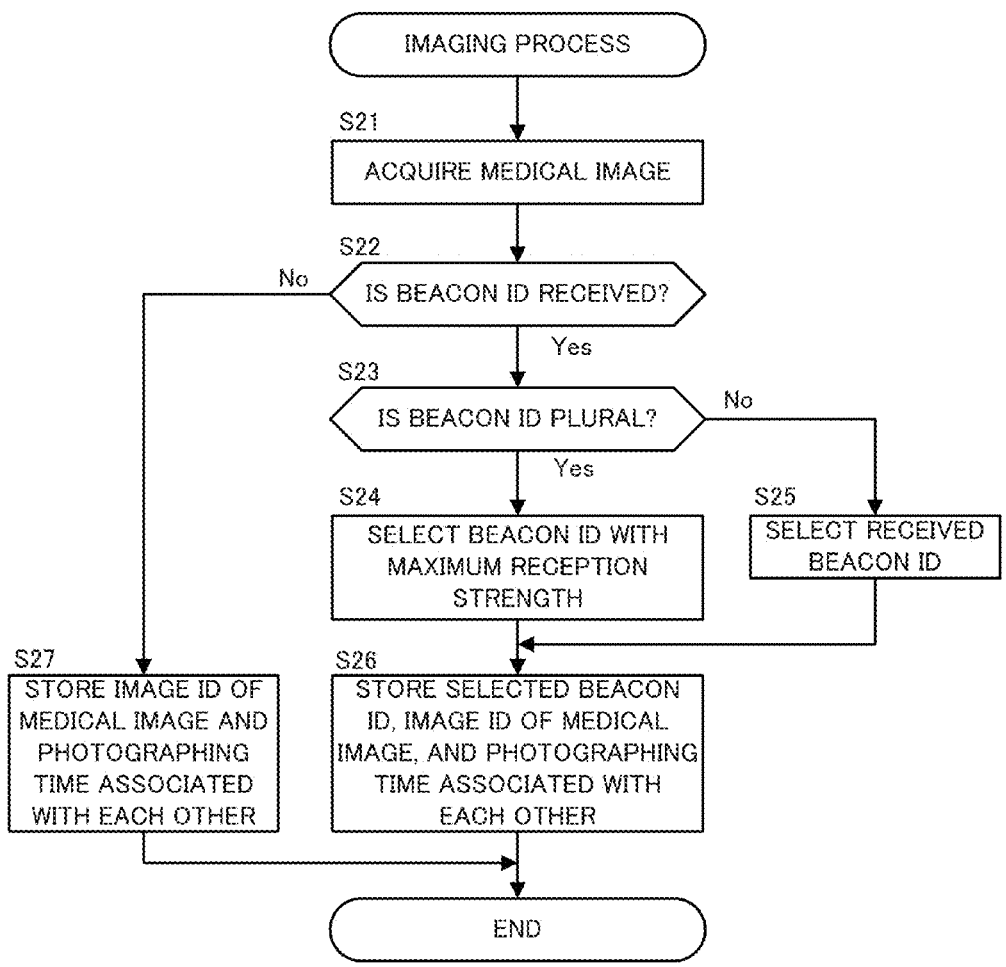

FIG. 12

CLASSIFICATION TABLE

| PATIENT ID | IMAGE ID |
|------------|----------|
| A | a |
| B | b |
| C | c |

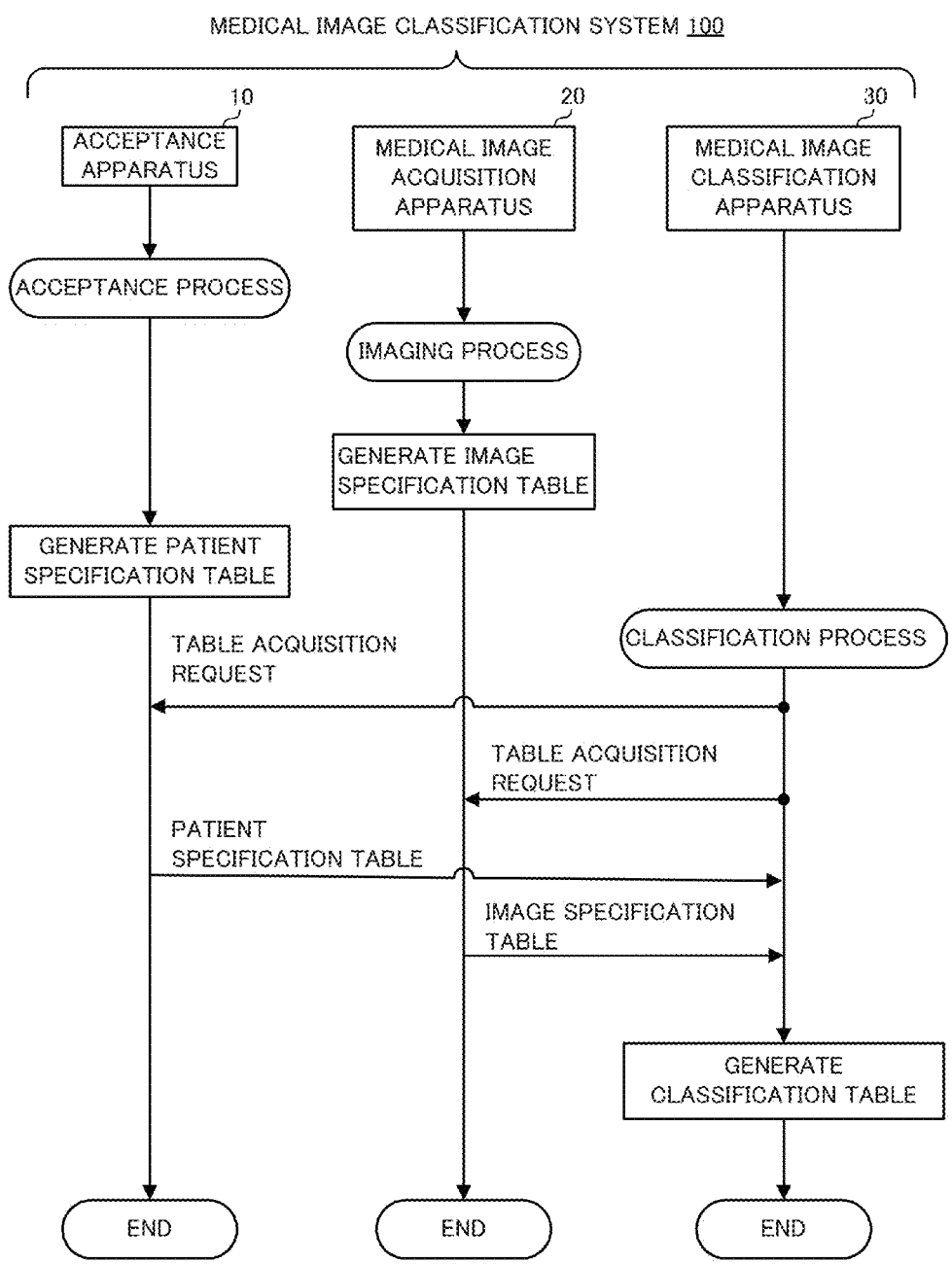

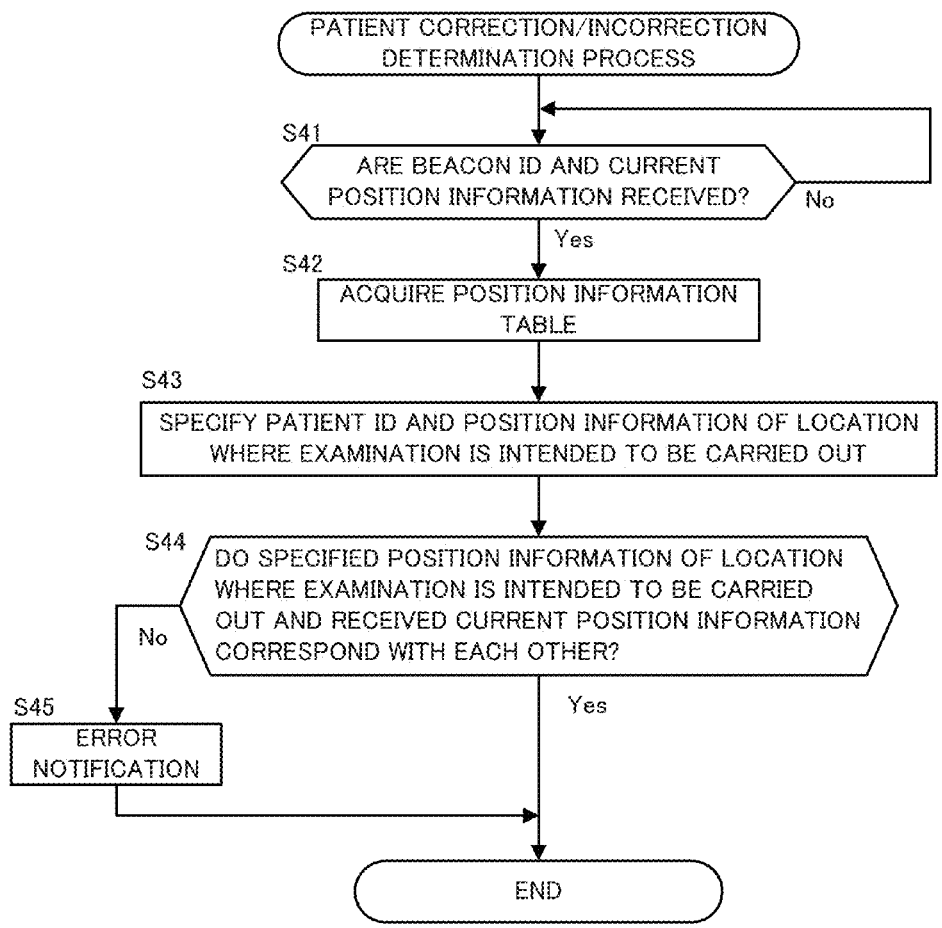

MEDICAL IMAGE CLASSIFICATION SYSTEM, MEDICAL IMAGE CLASSIFICATION METHOD, AND MEDICAL IMAGE CLASSIFICATION APPARATUS

CROSS-REFERENCE TO RELATED APPLICATION

This application is based upon and claims the benefit of priority under 35 USC 119 of Japanese Patent Application No. 2015-014838 filed on Jan. 28, 2015 the entire disclosure of which, including the description, claims, drawings, and abstract, is incorporated herein by reference in its entirety.

FIELD

The present disclosure relates to a medical image classification system, a medical image classification method, and a medical image classification apparatus which are preferably used in medical settings.

BACKGROUND

It is widely known that doctors diagnose the affected skin areas of patients using magnifying glasses such as dermoscopes in medical settings.

For example, Unexamined Japanese Patent Application Kokai Publication No. 2005-192944 discloses a remote diagnosis apparatus for the purpose of assisting a doctor to make a diagnosis. The remote diagnosis apparatus receives, via a network, a skin image photographed with a camera with a dermoscope by a doctor and transmits a diagnosis result of diagnosing the received skin image.

SUMMARY

A medical image classification system, including an acceptance apparatus, a medical image acquisition apparatus, and a medical image classification apparatus, the acceptance apparatus including:

an acceptor that accepts an input of patient identification information for identifying a patient and medium identification information of a portable information retaining medium carried by the patient; and a first storage that stores first association information in which the patient identification information and the medium identification information accepted by the acceptor are associated with each other;

the medical image acquisition apparatus including:

an identification information acquirer that acquires the medium identification information from the portable information retaining medium carried by the patient;

an image acquirer that acquires a medical image for diagnosing the patient; and a second storage that stores second association information in which medical image identification information for identifying the medical image acquired by the image acquirer and the medium identification information acquired by the identification information acquirer are associated with each other;

the medical image classification apparatus including:

a first acquirer that acquires the first association information stored by the first storage;

a second acquirer that acquires the second association information stored by the second storage; and a classifier that performs classification of the medical image identification information per the patient identification information based on the medium identification information in the first association information and the second association information.

The medical image classification system according to the present disclosure, wherein the first storage further stores a usage time period in which the patient carrying the portable information retaining medium uses the portable information retaining medium, associated with the patient identification information and the medium identification information, as the first association information;

the second storage further stores a photographing time at which the medical image is photographed, associated with the medical image identification information and the medium identification information, as the second association information;

the classifier includes:

a first determiner that determines whether or not the medium identification information in the second association information and the medium identification information in the first association information correspond with each other; and a second determiner that determines whether or not the photographing time in the second association information is within the usage time period in the first association information; and the classification is performed based on a determination result from the first determiner and the second determiner.

The medical image classification system according to the present disclosure, wherein the classifier assigns the medical image identification information to the patient identification information and performs the classification when the first determiner determines that the medium identification information in the second association information and the medium identification information in the first association information correspond with each other, and the second determiner determines that the photographing time is within the usage time period.

The medical image classification system according to the present disclosure, wherein the portable information retaining medium is a portable transmission medium; and the identification information acquirer includes receiver that receives medium identification information transmitted by the portable transmission medium.

The medical image classification system according to the present disclosure, wherein the medical image acquisition apparatus further includes selector that selects medium identification information with maximum reception strength when the receiver receives a plurality of items of medium identification information; and the second storage stores the second association information in which the medium identification information selected by the selector and the medical image identification information are associated with each other.

The medical image classification system according to the present disclosure, wherein the first storage further stores position information on a location at which a patient carrying the portable transmission medium intends to see a doctor, associated with the patient identification information and the medium identification information, as the first association information; and the medical image classification apparatus includes:

a position information receiver that receives medium identification information of the portable transmission medium, transmitted from the portable transmission medium carried by the patient, and current position information indicating a current position of the portable transmission medium;

a specifier that specifies the position information on the location at which the patient intends to see the doctor from the first association information acquired by the first acquirer based on the medium identification information received by the position information receiver; and a notifier that provides a notification that the patient is not at the location at which the patient intends to see the doctor when the position information on the location at which the patient intends to see the doctor, specified by the specifier, and the current position information received by the position information receiver do not correspond with each other.

The medical image classification system according to the present disclosure, wherein the medical image is a dermoscopy image of a patient, photographed through a dermoscope.

The medical image classification system according to the present disclosure, wherein the second storage is a non-transitory transportable storage medium.

The medical image classification system according to the present disclosure, wherein the portable transmission medium is a beacon in accordance with Bluetooth (registered trademark) Low Energy or a contactless IC card in accordance with Near Field Communication (NFC).

A medical image classification method, including:

an acceptance step of accepting an input of patient identification information for identifying a patient and medium identification information of a portable information retaining medium carried by the patient;

a first storage step of storing first association information in which the patient identification information accepted in the acceptance step and the medium identification information are associated with each other;

an identification information acquisition step of acquiring the medium identification information from the portable information retaining medium carried by the patient;

an image acquisition step of acquiring a medical image for diagnosing the patient;

a second storage step of storing second association information in which medical image identification information for identifying the medical image acquired in the image acquisition step and the medium identification information acquired in the identification information acquisition step are associated with each other;

a first acquisition step of acquiring the first association information stored in the first storage step;

a second acquisition step of acquiring the second association information stored in the second storage step; and a classification step of performing classification of the medical image identification information per the patient identification information based on the medium identification information in the first association information and the second association information.

A medical image classification apparatus, including:

a first acquirer that acquires first association information in which patient identification information for identifying a patient and medium identification information of a portable information retaining medium carried by the patient are associated with each other;

a second acquirer that acquires second association information in which medical image identification information for identifying a medical image for diagnosing the patient and medium identification information acquired from the portable information retaining medium are associated with each other; and a classifier that performs classification of the medical image identification information per the patient identification information based on the medium identification information in the first association information and the second association information.

A medical image classification method, including:

a first acquisition step of acquiring first association information in which patient identification information for identifying a patient and medium identification information of a portable information retaining medium carried by the patient are associated with each other;

a second acquisition step of acquiring second association information in which medical image identification information for identifying a medical image for diagnosing the patient and medium identification information acquired from the portable information retaining medium are associated with each other; and a classification step of performing classification of the medical image identification information per the patient identification information based on the medium identification information in the first association information and the second association information.

BRIEF DESCRIPTION OF THE DRAWINGS

A more complete understanding of this application can be obtained when the following detailed description is considered in conjunction with the following drawings, in which:

FIG. 5 is a drawing illustrating an example of the flowchart of an acceptance process;

FIG. 6 is a drawing illustrating an example of a patient specification table;

FIG. 8 is a drawing illustrating an example of the flowchart of an imaging process;

FIG. 9 is a drawing illustrating an example of an image specification table;

FIG. 12 is a drawing illustrating an example of a classification table;

FIG. 13 is a sequence diagram illustrating interactions between the corresponding apparatuses of a medical image classification system;

FIG. 14 is a drawing illustrating an example of a position information table; and FIG. 15 is a drawing illustrating an example of the flowchart of a patient correction/incorrection determination process.

DETAILED DESCRIPTION

Example embodiments of the present disclosure will be described below with reference to the drawings.

Figure 1:
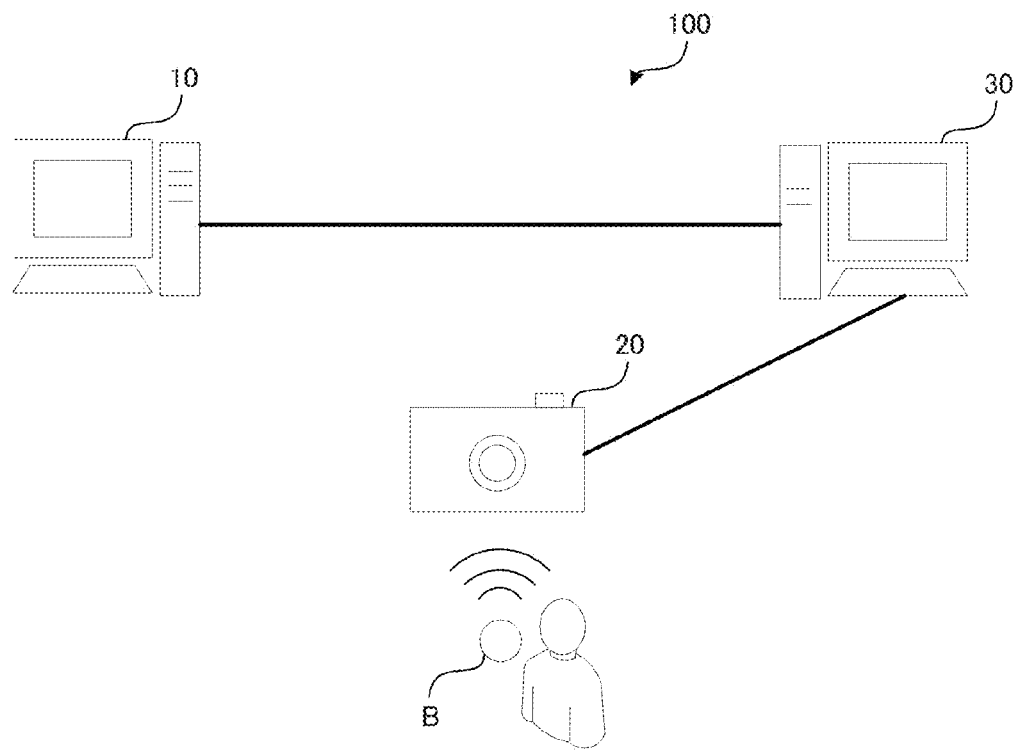
FIG. 1 is a drawing illustrating the configuration of a medical image classification system according to an example embodiment.

FIG. 1 is a drawing illustrating the configuration of a medical image classification system according to an example embodiment of the present disclosure.

The medical image classification system illustrated in FIG. 1 comprises an acceptance apparatus 10, a medical image acquisition apparatus 20, and a medical image classification apparatus 30.

The acceptance apparatus 10, which is, for example, a personal computer (PC), is connected to the medical image classification apparatus 30 via a cable (such as a local area network (LAN) cable) and accepts various items of information based on a user operation.

The medical image acquisition apparatus 20, which is, for example, a camera, can communicate with the medical image classification apparatus 30 via a cable (such as a universal serial bus (USB) cable). The medical image acquisition apparatus 20 can receive information transmitted by a beacon B.

The beacon B, which is a portable transmission medium that can be carried by a user, transmits various items of information to the neighborhood of the beacon B. In the present example embodiment, as an example, the beacon B transmits a beacon ID for self-identification based on Bluetooth (registered trademark) Low Energy (hereinafter referred to as "BLE") which is a short-range wireless communication standard with reduced power consumption. The medical image acquisition apparatus 20 supports the short-range wireless communication standard and receives the beacon ID transmitted by the beacon B based on BLE.

The medical image classification apparatus 30, which is, for example, a PC, performs classification based on each information acquired from the acceptance apparatus 10 and the medical image acquisition apparatus 20. Specifically, the medical image classification apparatus 30 acquires an item of information according to a user of the beacon B from the acceptance apparatus 10, acquires an item of information according to a medical image from the medical image acquisition apparatus 20, and links the items of information based on the beacon ID of the beacon B, to perform a classification process. The details of the classification process will be described later.

A case in which a medical image classification system 100 comprising such corresponding apparatuses (acceptance apparatus 10, medical image acquisition apparatus 20, and medical image classification apparatus 30) is applied to a medical setting is described below as an example. In this example, a user of the acceptance apparatus 10 is a hospital receptionist (for example, a medical clerk or the like), a user of the medical image acquisition apparatus 20 and the medical image classification apparatus 30 is a doctor, and a user of a beacon B is a patient.

In advance of specific descriptions of each apparatus, the medical image acquisition apparatus 20 used for a diagnosis by the doctor in the medical setting as a premise, a photographed medical image, and the like will be described.

Figure 2:
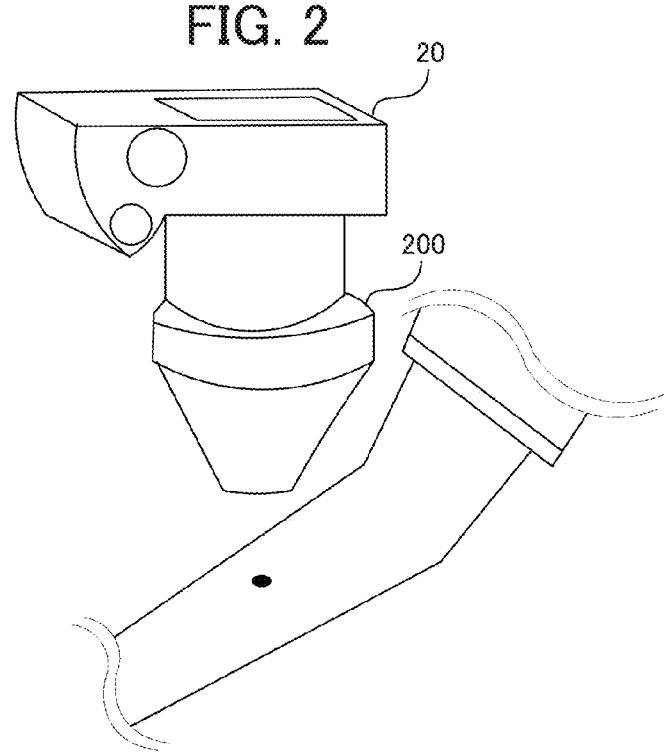
FIG. 2 is a drawing illustrating a scene of a dermoscopy diagnosis.

FIG. 2 is a drawing illustrating a scene of a dermoscopy diagnosis. The dermoscopy diagnosis is a diagnosis using a dermoscope 200 with which an affected skin area is observed under a magnification of 10 to 30 times. The dermoscope 200 is a magnifying glass comprising: a light source such as a halogen lamp or a white light emitting diode (LED); and a polarization filter that reduces reflected light. As illustrated in the drawing, the dermoscope 200 is used in the state of being mounted on the medical image acquisition apparatus 20 via an attachment or the like.

The dermoscopy diagnosis enables a doctor to diagnose an affected skin area with a pigment distribution between the epidermis and upper dermis of the skin under magnification because any irregular reflection caused by the keratin of the skin does not occur.

Figure 3:
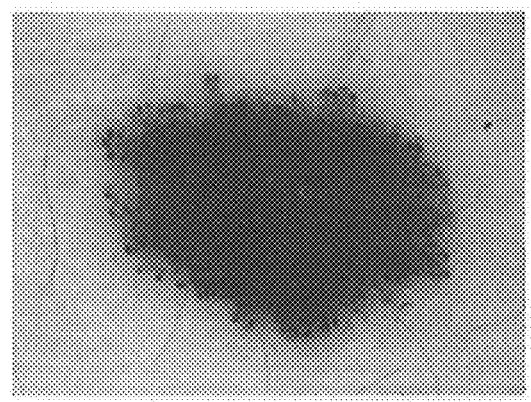
FIG. 3 is a drawing illustrating an example of a dermoscopy image.

The doctor specifies the affected skin area of a patient and photographs the affected skin area with the medical image acquisition apparatus 20 with the dermoscope 200. FIG. 3 illustrates an example of a dermoscopy image which is an image photographed with the dermoscope 200. By observing an affected skin area in the dermoscopy image, the doctor can diagnose, for example, whether the affected skin area is benign (lentigo or the like) or malignant (melanoma or the like).

In the present embodiment, the medical image classification system 100 is applied to a medical setting in which a dermoscopy diagnosis is made, and the dermoscopy images of patients, photographed with the dermoscope 200, are automatically classified per patient.

On the premise of the above medical setting, the specific configuration of each apparatus (acceptance apparatus 10, medical image acquisition apparatus 20, and medical image classification apparatus 30) of the medical image classification system 100 will be described one by one.

Figure 4:
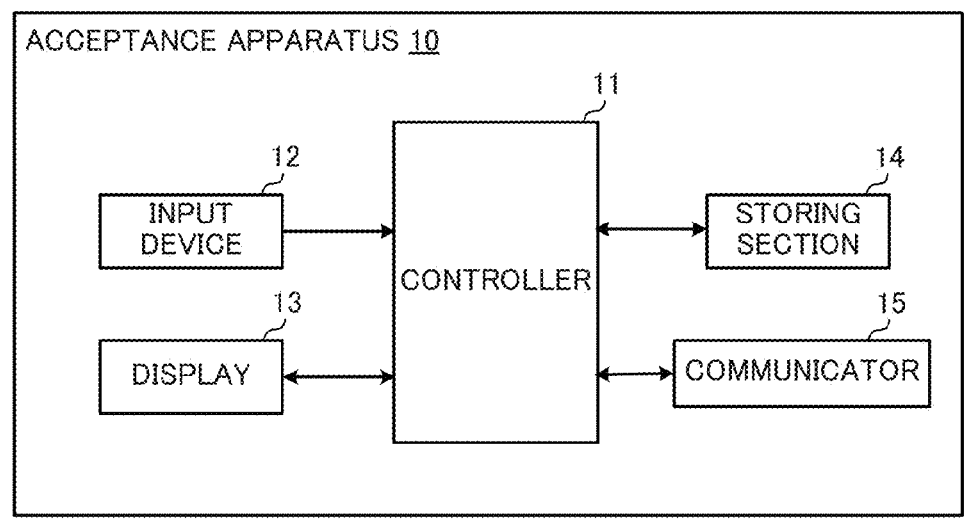
FIG. 4 is a block diagram illustrating the configuration of an acceptance apparatus according to an example embodiment.

First, the configuration of the acceptance apparatus 10 is described with reference to FIG. 4. The acceptance apparatus is placed at a hospital reception desk and accepts the inputs of various items of information from a medical clerk.

The acceptance apparatus 10 comprises a controller 11, an input device 12, a display 13, a storing section 14, and a communicator 15.

The controller 11 comprises, for example, a central processing unit (CPU), a read only memory (ROM), and/or the like. The controller 11 implements the various functions (such as an acceptance process described later) of the acceptance apparatus 10 by control according to a program stored in the ROM. The controller 11 corresponds to an acceptor.

The input device 12 comprises, for example, a keyboard, a mouse, and/or the like, and is used in order for a user to input an operation content.

The display 13 comprises, for example, a liquid crystal display (LCD), an electroluminescence (EL) display, and/or the like. According to control by the controller 11, the display 13 displays a screen used in order for a medical clerk to input information.

The storing section 14 comprises a nonvolatile memory such as a hard disk drive (HDD) and stores data and a table (such as a patient specification table described later). The storing section 14 corresponds to a first storage.

The communicator 15 is a communication interface for communicating with an external apparatus. The controller 11 communicates with the medical image classification apparatus 30 via the communicator 15.

The controller 11 of the acceptance apparatus 10 comprising each component described above executes an acceptance process by controlling each component as appropriate according to the program stored in the ROM. The acceptance process will be described with reference to FIG. 5. The acceptance process starts when the medical clerk, after having accepted a patient visiting a hospital and after having lent the patient a beacon B, inputs a patient ID, the beacon ID of the lent beacon B, and the lending time, using the input device 12.

In expectation of the peak number of patients visiting the hospital, beacons B corresponding to the number of the patients are prepared in advance at a reception desk. The medical clerk lends a patient one beacon B optionally selected from the plural beacons B each time accepting the patient visiting the hospital. The medical clerk inputs information (patient ID, beacon ID, and lending time) into the acceptance apparatus 10.

First, the controller 11 accepts the inputs of the patient ID, the beacon ID, and the lending time (step S11). Specifically, the controller 11 accepts the inputs of the patient ID for identifying the patient, the beacon ID for identifying the beacon B lent to the patient, and the lending time at which the beacon B is lent to the patient.

Then, the controller 11 determines whether or not to accept the input of the time of the return of the lent beacon B (step S12). The controller 11 waits until the input of the return time is accepted (step S12; No). During this period, the patient possessing the beacon B has an examination by a doctor. When the patient coming back to the reception desk after the examination returns the beacon B to the medical clerk, the medical clerk inputs the return time into the acceptance apparatus 10.

When the acceptance apparatus 10 accepts the input of the return time (step S12; Yes), the controller 11 calculates a usage time period in which the beacon B is used from the lending time and the return time (step S13) and stores the patient ID, the beacon ID, and the usage time period associated with each other (step S14). Specifically, the controller 11 stores, in the storing section 14, the patient ID, the beacon ID, and the usage time period associated with each other. After step S14, the acceptance process is ended.

The storing section 14 stores a patient specification table (see FIG. 6) in which patient IDs, beacon IDs, and usage time periods in which beacons are used, which are associated with each other, by repeating such an acceptance process each time an input from the medical clerk is accepted.

The patient specification table reveals that a beacon 1 having a beacon ID of 1 is used in a patient having a patient ID of A (patient A) and a patient having a patient ID of C (patient C) in different usage time periods. In such a manner, the usage history of a beacon based on each patient can be confirmed on a time period basis from the patient specification table. When it is not necessary to specially specify and describe any of beacons (such as beacons 1 and 2), a beacon B is typically described below. Similarly, when it is not necessary to specially specify and describe any of patients (such as patients A and B), a patient is typically described below.

Figure 7:
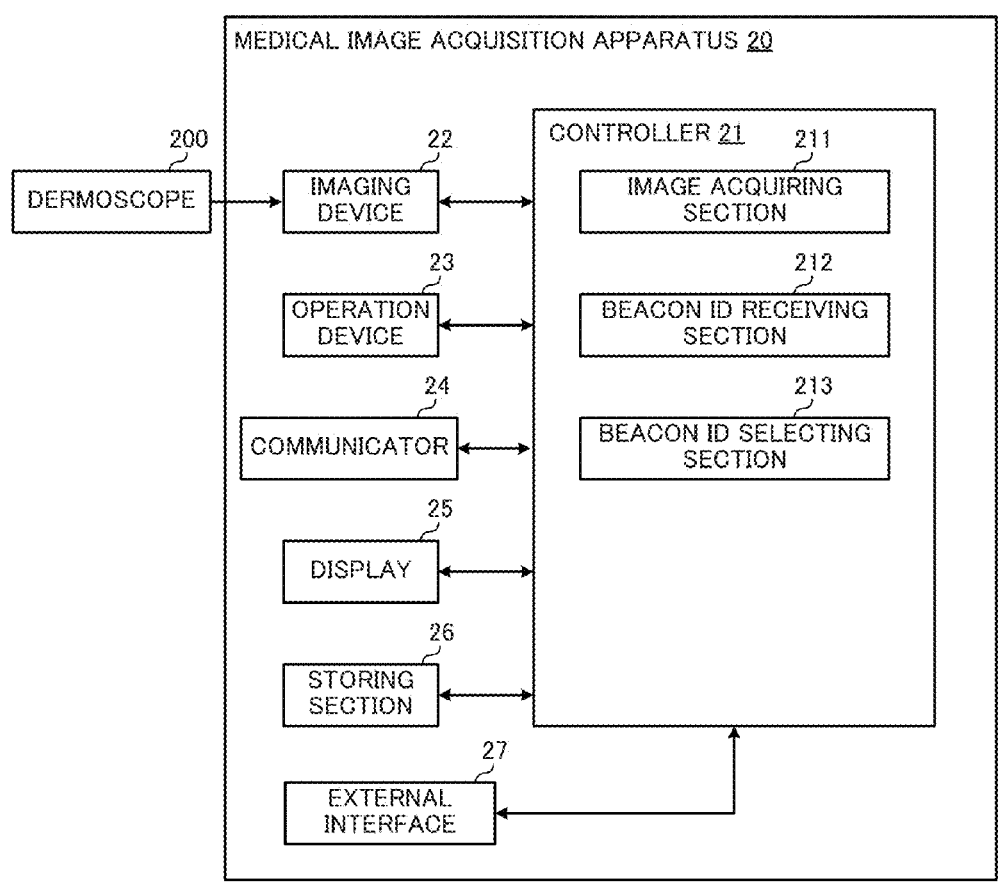
FIG. 7 is a block diagram illustrating the configuration of a medical image acquisition apparatus according to an example embodiment.

The configuration of the medical image acquisition apparatus 20 will be described below with reference to FIG. 7. The medical image acquisition apparatus 20, which is a camera used during an examination by a doctor, acquires a dermoscopy image which is a medical image.

The medical image acquisition apparatus 20 comprises a controller 21, an imaging device 22, an operation device 23, a communicator 24, a display 25, a storing section 26, and an external interface 27.

The controller 21 comprises, for example, a CPU, a ROM, and/or the like. The controller 21 implements the function of each component (image acquiring section 211, beacon ID receiving section 212, and beacon ID selecting section 213) by control according to a program stored in the ROM. The function of each of the components will be described later.

The imaging device 22 comprises an optical element such as a lens or a diaphragm; and an image sensor such as a charge coupled device (CCD) or a complementary metal oxide semiconductor (CMOS). By a user (doctor) operation, the affected skin area of a patient, enlarged by the dermoscope 200, is photographed with the imaging device 22.

The operation device 23 comprises various buttons. Examples of the various buttons include a shutter button for instructing a photographing operation and function buttons for making various settings.

The communicator 24 is an interface for performing short-range wireless communication based on BLE. Via the communicator 24, the controller 21 receives a beacon ID transmitted by the beacon B.

The display 25 comprises, for example, an LCD, an EL display, and/or the like. The display 25 provides an output to display a live view imaging in real time a photographed image made by the imaging device 22, a photographed dermoscopy image, or the like.

The storing section 26, which is a non-transitory transportable storage medium such as a secure digital (SD) card, stores a dermoscopy image and a table (such as an image specification table described later). The storing section 26 corresponds to a second storage.

The external interface 27 comprises a USB connector, a video output terminal, and/or the like. Via a USB cable and/or the like, the controller 21 outputs a dermoscopy image to the medical image classification apparatus 30 and provides an output to display the dermoscopy image to a display 35 in the medical image classification apparatus 30.

The controller 21 may output a dermoscopy image to the medical image classification apparatus 30 by short-range wireless communication based on BLE, without limitation to wire communication via the external interface 27.

The function of each component (image acquiring section 211, beacon ID receiving section 212, and beacon ID selecting section 213) of the controller 21 will be described below.

The image acquiring section 211 acquires a medical image for diagnosing a patient. Specifically, the image acquiring section 211 acquires the dermoscopy image of the patient, photographed with the dermoscope 200 by the imaging device 22. The image acquiring section 211 corresponds to an image acquirer.

The beacon ID receiving section 212 receives the beacon ID of the beacon B, transmitted from the beacon B. The beacon ID receiving section 212 corresponds to a receiver.

The beacon ID selecting section 213 selects a beacon ID with the maximum reception strength when the beacon ID receiving section 212 receives a plurality of beacon IDs. A specific selection process carried out by the beacon ID selecting section 213 will be described later. The beacon ID selecting section 213 corresponds to a selector.

The controller 21 of the medical image acquisition apparatus 20 comprising each component described above executes an imaging process by controlling each component as appropriate according to the program stored in the ROM. The imaging process will be described with reference to FIG. 8. The imaging process is started when a doctor specifies an affected skin area to push down the shutter button of the operation device 23 while examining the skin of a patient possessing a beacon B.

First, the image acquiring section 211 acquires a medical image (step S21). Specifically, the image acquiring section 211 acquires a dermoscopy image showing the affected skin area of the patient, photographed by the doctor.

Then, the beacon ID receiving section 212 determines whether or not to receive a beacon ID (step S22). Specifically, the beacon ID receiving section 212 determines whether or not to receive the beacon ID transmitted from the beacon B by short-range wireless communication based on BLE.

When determining that the beacon ID is received (step S22; Yes), the beacon ID receiving section 212 determines whether the received beacon ID is plural or not (step S23). When the beacon ID is not plural (step S23; No), that is, when only the beacon ID transmitted from the beacon B possessed by the patient who is being examined is received, the beacon ID selecting section 213 selects the received beacon ID (step S25).

Alternatively, when the beacon ID is plural (step S23; Yes), that is, when any beacon ID other than the beacon ID transmitted from the beacon B possessed by the patient who is being examined (for example, a beacon ID transmitted from a beacon B possessed by another patient in a waiting room) is also received, the beacon ID selecting section 213 selects a beacon ID with the maximum reception strength (step S24). As a result, the beacon ID transmitted from the beacon B possessed by the patient who is being examined by the doctor can be selected.

The reason that the beacon ID with the maximum reception strength is selected is because the patient possessing the beacon B transmitting the beacon ID with the maximum reception strength is assumed to be nearest to the doctor. However, practically, it is conceivable that there is a case in which the above assumption does not hold due to various situations. Examples of the case include a case in which a waiting room is near and the reception strength of a beacon ID transmitted from the waiting room is stronger; a case in which transmission strength is changed due to the state of the battery drain of each of a plurality of beacons B, so that levels of reception strength vary; and the like. It will be appreciated that in an actual setting, confirmation by a doctor is needed and precision can be increased by using Near Field Communication (NFC) or Global Positioning System (GPS) described later.

After step S24 or S25, the controller 21 allows the selected beacon ID, the image ID of the medical image, and a photographing time associated with each other to be stored. Specifically, the controller 21 allows the selected beacon ID, the image ID for identifying the photographed dermoscopy image, the photographing time at which the dermoscopy image is photographed, associated with each other, to be stored in the storing section 26 (step S26).

By repeating the imaging process each time the doctor pushes down the shutter button, the storing section 26 stores an image specification table in which the image IDs of dermoscopy images, selected beacon IDs, and photographing times are associated with each other (see FIG. 9). An entry in the image specification table is accompanying information (Exchangeable Image File Format (Exif)) that accompanies one dermoscopy image. Thus, the image specification table can also be considered to be a table in which items of accompanying information that accompany corresponding dermoscopy images are gathered.

The image specification table reveals that for example, the dermoscopy image with an image ID of a is photographed at 9:40, and the beacon ID received at the time of the photographing is 1.

In such a manner, a beacon ID associated with each image ID is managed in the image specification table.

Referring back to FIG. 8, in a case in which the beacon ID is not received in step S22 (step S22; No), that is, in such a case that the patient who is being examined does not possess the beacon B, the controller 21 allows the image ID of the medical image and the photographing time associated with each other to be stored (step S27). In this case, the controller 21 allows the beacon ID to be stored in the storing section 26 separately from the image specification table because the beacon ID is not able to be associated.

In step S27, the controller 21 may provide together by voice and/or the like an error notification that it is impossible to receive the beacon ID. The error notification is effective in such a case that a patient forgets borrowing a beacon B at a reception desk.

After step S26 or 27, the imaging process is ended. After ending the examination by the doctor, the patient returns the beacon B at the reception desk, and the medical clerk inputs into the acceptance apparatus 10 a time at which the beacon B is returned.

Figure 10:
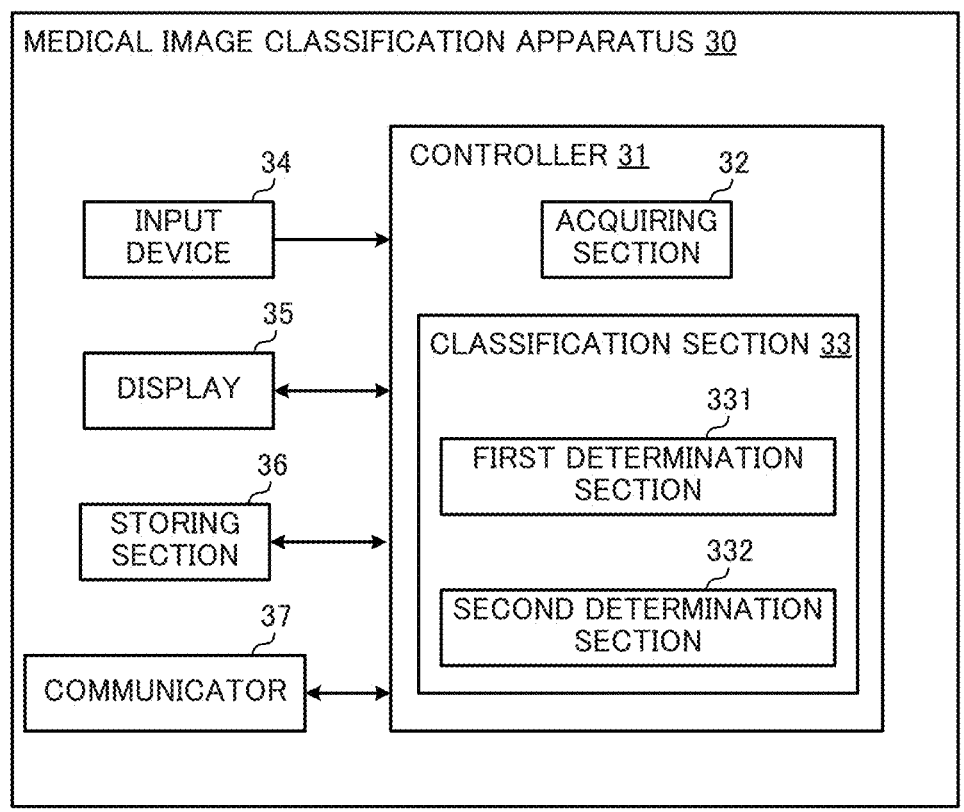
FIG. 10 is a block diagram illustrating the configuration of a medical image classification apparatus according to an example embodiment.

The configuration of the medical image classification apparatus 30 will be described below with reference to FIG. 10. The medical image classification apparatus 30 is placed in the examination room of the doctor and classifies dermoscopy images per patient based on the patient specification table and image specification table that are acquired.

The medical image classification apparatus 30 comprises a controller 31, an input device 34, the display 35, a storing section 36, and a communicator 37.

The controller 31 comprises, for example, a CPU, a ROM, and/or the like. The controller 31 implements the function of each component (acquiring section 32 and classification section 33) by control according to a program stored in the ROM. The function of each of the components will be described later.

The input device 34 comprises, for example, a keyboard, a mouse, and/or the like, and is used in order for a user to input an operation content.

The display 35 comprises, for example, an LCD, an EL display, and/or the like. According to control by the controller 31, the display 35 provides an output to display a dermoscopy image acquired from the medical image acquisition apparatus 20.

The storing section 36 comprises a nonvolatile memory such as an HDD and stores a dermoscopy image and a table (such as a classification table described later).

The communicator 37 is a communication interface for communicating with an external apparatus. The controller 31 communicates with the acceptance apparatus 10 and the medical image acquisition apparatus 20 via the communicator 37.

The function of each component (acquiring section 32 and classification section 33) of the controller 31 will be described below.

The acquiring section 32 acquires the patient specification table and the image specification table. Specifically, the acquiring section 32 acquires, via the communicator 37, the patient specification table stored in the storing section 14 of the acceptance apparatus 10 and the image specification table stored in the storing section 26 of the medical image acquisition apparatus 20.

An acquisition method is optional. It is necessary only that for example, the acquiring section 32 of the medical image classification apparatus 30 transmits table acquisition requests to the acceptance apparatus 10 and the medical image acquisition apparatus 20, respectively, and receives the patient specification table and image specification table transmitted in response to the requests. Alternatively, each of synchronization between the medical image classification apparatus 30 and the acceptance apparatus 10, or synchronization between the medical image classification apparatus 30 and the medical image acquisition apparatus 20 may be automatically achieved at a predetermined interval.

The acquiring section 32 also acquires a dermoscopy image specified by each image ID from the medical image acquisition apparatus 20 in timing with the acquisition of the image specification table. The acquiring section 32 corresponds to a first acquirer and a second acquirer.

The classification section 33 comprises a first determination section 331 and a second determination section 332, and classifies each image ID per patient ID based on the patient specification table and image specification table acquired by the acquiring section 32. The classification section 33 corresponds to a classifier.

The first determination section 331 determines whether or not the beacon IDs in the image specification table and the beacon IDs in the patient specification table are corresponded with each other. The first determination section 331 corresponds to a first determiner.

The second determination section 332 determines whether or not the photographing times in the image specification table are within the corresponding usage time periods in the patient specification table. The second determination section 332 corresponds to a second determiner.

Figure 11:
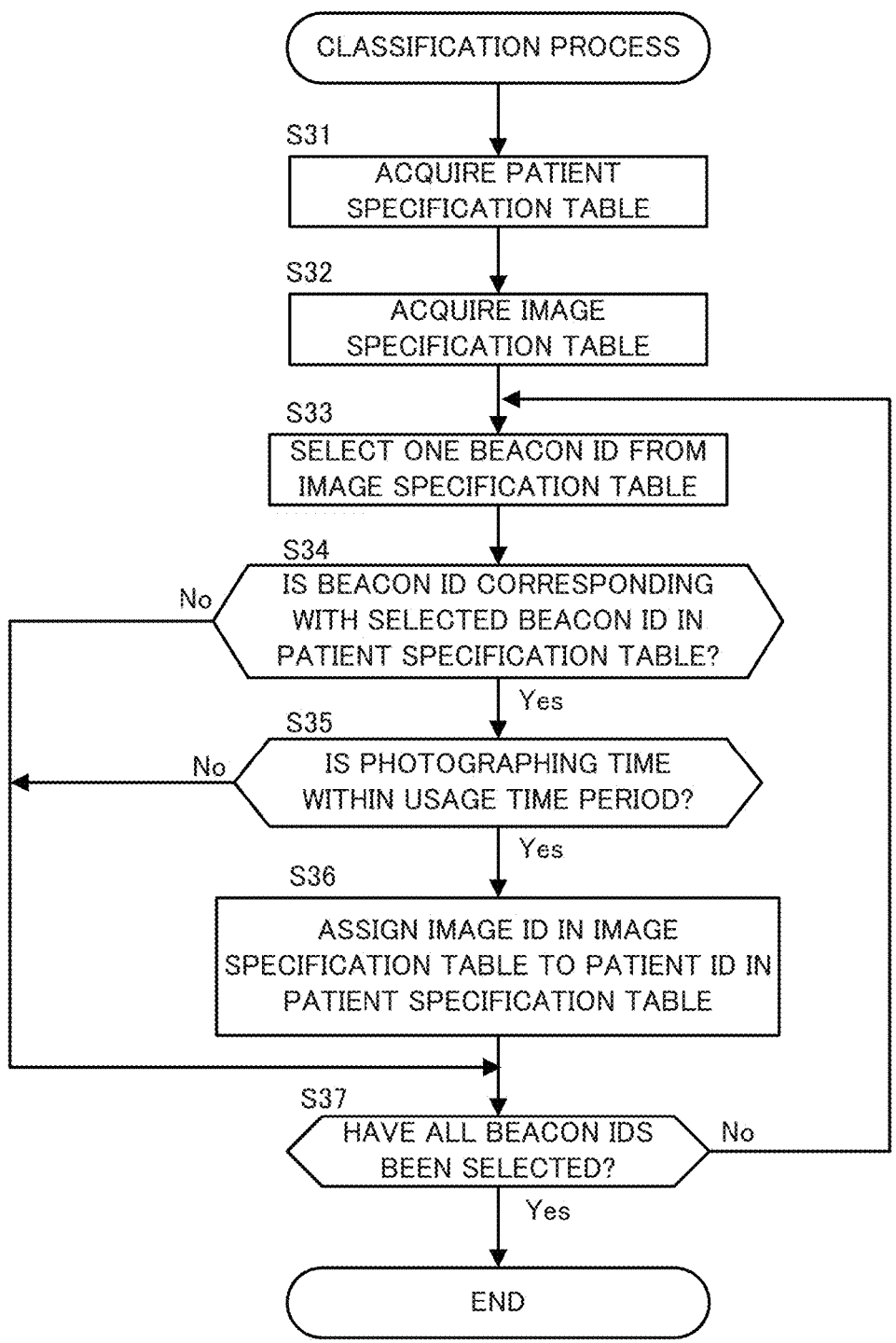
FIG. 11 is a drawing illustrating an example of the flowchart of a classification process.

The controller 31 of the medical image classification apparatus 30 comprising each component described above executes a classification process by controlling each component as appropriate according to the program stored in the ROM. The classification process will be described with reference to FIG. 11. The classification process is started when a doctor provides, via the input device 34, an instruction to execute the classification process.

First, the acquiring section 32 acquires the patient specification table (step S31). Specifically, the acquiring section 32 acquires the patient specification table transmitted from the acceptance apparatus 10 in response to the table acquisition request.

Then, the acquiring section 32 acquires the image specification table (step S32). Specifically, the acquiring section 32 acquires the image specification table transmitted from the medical image acquisition apparatus 20 in response to the table acquisition request.

The order in which the patient specification table and the image specification table are acquired does not matter because it is necessary only that the patient specification table and the image specification table are acquired prior to the process according to the classification in step S33 or later. Thus, the order of step S31 and step S32 may be reversed, or the patient specification table and the image specification table may be simultaneously acquired.

Then, the classification section 33 selects one beacon ID from the image specification table (step S33). For example, the classification section 33 selects the beacon ID of 1 of the image ID of a from the image specification table illustrated in FIG. 9.

Then, the first determination section 331 determines whether or not the beacon ID corresponding with the selected beacon ID is in the patient specification table (step S34). Specifically, the first determination section 331 compares the selected beacon ID with the beacon ID of each row in the patient specification table on a one-by-one basis, to specify all corresponding beacon IDs. For example, the first determination section 331 specifies, as beacon IDs corresponding with the beacon ID of 1, a beacon ID of 1 with a patient ID of A and a beacon ID of 1 with a patient ID of C from the patient specification table.

When it is determined that the beacon ID corresponding with the selected beacon ID is in the patient specification table (step S34; Yes), that is, when at least one corresponding beacon ID is specified, the second determination section 332 determines whether or not the photographing time is within the usage time period (step S35). Specifically, the second determination section 332 determines whether or not the photographing time associated with the selected beacon ID is within the usage time period of the beacon associated with the beacon ID determined to correspond with the selected beacon ID.

For example, it is determined whether or not a photographing time of 9:40 associated with a selected beacon ID of 1 is within each of the usage time periods of 9:00 to 10:00 and 10:05 to 10:30 of beacons associated with beacon IDs of 1 determined to correspond with the selected beacon ID of 1.

When the photographing time is within the usage time period (step S35; Yes), the classification section 33 assigns the image ID in the image specification table to the patient ID in the patient specification table (step S36). Specifically, when the first determination section 331 determines that the beacon IDs correspond with each other and when the second determination section 332 determines that the photographing time is within the usage time period, the classification section 33 assigns the image ID in the image specification table to the patient ID in the patient specification table and allows the IDs to be stored in the storing section 36.

For example, the classification section 33 assigns an image ID of a to a patient ID of A with a beacon ID of 1 determined to correspond with a selected beacon ID of 1 by the first determination section 331 and with a usage time period of 9:00 to 10:00 within which the photographing time of 9:40 of the beacon ID of 1 is determined to be by the second determination section 332, and allows the IDs to be stored in the storing section 36.

The processing order of step S34 and step S35 may be reversed because the assignment can be carried out even if the processing order is reversed.

Alternatively, when the beacon ID corresponding with the selected beacon ID is not in the patient specification table (step S34; No), or when the photographing time is not within the usage time period although the corresponding beacon ID is in the patient specification table (step S35; No), the assignment is impossible, and therefore, step S36 is skipped to step S37.

In step S37, the classification section 33 determines whether or not all the beacon IDs in the image specification table have been already selected (step S37). If all the beacon IDs have not been selected (step S37; No), the classification section 33 returns back to step S33 and selects one beacon ID from unselected beacon IDs. In the case of the above-described example, a beacon ID (for example, a beacon ID of 2 with an image ID of b) other than the beacon ID of 1 with the image ID of a is selected to carry out processes of step S34 to step 36.

In such a manner, the classification section 33 assigns an image ID to a patient ID based on one selected beacon ID (loop of step S33 to step S37) until all the beacon IDs are selected, and the classification process is ended when all the beacon IDs are selected (step S37; Yes).

By carrying out the classification process, the classification table in which the patient IDs and the image IDs are associated with each other, that is, in which the image IDs are classified per patient ID is stored in the storing section 36 (see FIG. 12). Because dermoscopy images are specified by the image IDs, the classification table can also be considered to be a table in which the dermoscopy images are classified per patient examined by the doctor.

The interactions between the respective apparatuses (acceptance apparatus 10, medical image acquisition apparatus 20, and medical image classification apparatus 30) of the medical image classification system 100 described above will be mainly described below with reference to FIG. 13. As an example, a case in which a patient A visits a hospital and is handed a beacon 1 by a medical clerk is described as appropriate.

First, the acceptance apparatus 10 carries out the acceptance process described above. For example, the acceptance apparatus 10 accepts a patient ID of A of which the input has been accepted, a beacon ID of 1, and a lending time, and waits until accepting a return time.

Meanwhile, the patient A receives a dermoscopy diagnosis made by a doctor. When the doctor pushes down the shutter button of the medical image acquisition apparatus 20, the medical image acquisition apparatus 20 carries out the imaging process described above and generates an image specification table (image ID of a, beacon ID of 1, and photographing time of 9:40, as a first entry) to end the process.

It is assumed that the patient A finishes the diagnosis and returns the beacon 1 to a reception desk, and the medical clerk inputs the return time. Then, the acceptance apparatus 10 generates a patient specification table (patient ID of A, beacon ID of 1, and usage time period of beacon of 9:00 to 10:00, as a first entry) in the acceptance process described above, to end the process.

When the doctor provides, via the input device 34 of the medical image classification apparatus 30, an instruction to execute a classification process, the medical image classification apparatus 30 executes the classification process described above, transmits table acquisition requests to the acceptance apparatus 10 and the medical image acquisition apparatus 20, respectively, and acquires the patient specification table and the image specification table transmitted in response to the requests.

Then, the medical image classification apparatus 30 generates a classification table (patient ID of A and image ID of a, as a first entry) based on the tables, to end the process. As a result, the patient A and a dermoscopy image with the image ID of a are automatically associated with each other. When there are a plurality of entries in the patient specification table and the image specification table, dermoscopy images are classified per patient.

According to the medical image classification system 100 described above with reference to FIG. 4 to FIG. 13, the dermoscopy images can be automatically classified per patient based on the beacon IDs and the time information in each of the tables (patient specification table and image specification table) generated by the acceptance apparatus 10 and the medical image acquisition apparatus 20, respectively. Thus, the medical image classification system 100, according to the present example embodiment, can reduce a workload pertaining to the classification.

Information that specifies a patient (for example, patient ID) is not stored in the image specification table stored in the storing section 26 (non-transitory transportable storage medium such as SD card) of the medical image acquisition apparatus 20 in the present example embodiment. Thus, the personal information of a patient does not leak out even if an outsider runs away with the storing section 26 for illicit purposes. As a result, compliance with the Health Insurance Portability and Accountability Act (HIPAA) that provides privacy rules for the health information of patients in U.S.A. can be achieved.

In the medical image classification system 100 in the present example embodiment, a plurality of beacons B are repeatedly used by managing usage time periods in which the beacons B are used (in other words, it is not necessary to prepare a beacon corresponding to each patient). Thus, it is necessary only to prepare in advance beacons corresponding to the on-peak number of patients visiting a hospital, and the number of beacons can be therefore reduced. Further, because it is not necessary to manage a beacon in association with each patient, the load of managing a plurality of beacons can be reduced, and a beacon can be easily replaced with another beacon when the beacon is lost. However, it is also possible to prepare in advance beacons corresponding to patients, respectively.

For example, dermoscopy images can be classified per patient based only on beacon IDs regardless of time (determination whether or not a photographing time is within a usage time period) by associating a beacon with each patient, that is, by associating a beacon ID with each patient ID. Thus, a process load according to classification by the medical image classification apparatus 30 can be reduced.

In the example embodiment described above, the medical image acquisition apparatus 20 transmits dermoscopy images and an image specification table to the medical image classification apparatus 30 by wired communication (such as USB cable) or wireless communication (such as BLE), without limitation thereto. For example, a user may pull out the storing section 26 (SD card) and may insert the storing section 26 into the medical image classification apparatus 30, to thereby transfer the dermoscopy images and the image specification table to the medical image classification apparatus 30.

Further, the example embodiment is described above based on the premise that the portable transmission medium carried by a patient is a beacon, without limitation thereto. For example, the portable transmission medium may be a contactless IC card in accordance with NFC. In this case, the patient carries the non-contact integrated circuit (IC) card and receives a diagnosis by a doctor. Then, the contactless IC card receives weak electric waves from a reader/writer included in the medical image acquisition apparatus 20, is booted by electromagnetic induction, and transmits a card ID to the medical image acquisition apparatus 20. In such a manner, the contactless IC card can be used instead of a beacon B.

Furthermore, the medical image acquisition apparatus 20 may acquire a card ID in a contact manner with the use of an SD card, a magnetic card, or the like which is a portable information retaining medium. In this case, for example, a user who carries the magnetic card may bring the magnetic card in contact with the medical image acquisition apparatus 20 to acquire the card ID. In this case, the beacon ID receiving section 212 of the medical image acquisition apparatus 20 functions as an identification information acquirer that acquires the medium identification information of the portable information retaining medium (for example, acquires the card ID of the magnetic card). The portable information retaining medium is a superordinate concept of a portable transmission medium, and is not limited only to contact-type media such as magnetic cards and SD cards but also encompasses non-contact-type media such as beacons and FeliCa.

Further, in the example embodiment described above, a medical clerk who is a user for the acceptance apparatus 10 inputs a patient ID, a beacon ID, and a lending time into the acceptance apparatus 10 when accepting a patient, without limitation thereto. It is also acceptable that the medical clerk inputs a patient ID and a beacon ID and that the acceptance apparatus 10 regards a time at which the patient ID and the beacon ID are accepted as a lending time and automatically associates the lending time, the patient ID, and the beacon ID with each other. Further, the medical clerk need not input a return time, but it is necessary only that the fact that a beacon B is returned is input into the acceptance apparatus 10. For example, it is necessary only that when a beacon 1 lent to a patient A is returned, the medical clerk pushes down a "returned" button for the beacon 1 displayed on the display 13 of the acceptance apparatus 10.

In this case, in the acceptance process in FIG. 5, when the acceptance apparatus 10 accepts the inputs of the patient ID and the beacon ID (step S11), the current time of the acceptance as the lending time is associated with the patient ID and the beacon ID. Then, when the acceptance apparatus 10 accepts the return of the beacon B (step S12; Yes), the current time of the acceptance is regarded as the return time, and a usage time period is calculated from the lending time and the return time. In such a manner, the workload of the inputs of times on a medical clerk can be reduced.

The example embodiment has been described above. However, it will be appreciated that the example embodiment described above is an example, and the configuration of the medical image classification system 100, the content of the process carried by each apparatus, and the like are not limited to the descriptions of the example embodiment described above.

Alternative Example Embodiment

The example embodiment is described above based on the premise that a patient does not go to a wrong examination location. However, it is practically possible that a patient goes to another wrong examination location and a doctor mistakenly believes the patient to be a patient to be examined and diagnoses the patient. Thus, in a medical image classification system 100' in an alternative example, a beacon B is provided with a GPS function, which is the function of specifying the current position of a patient and determining whether or not the patient is at an examination location where the patient should be examined. The function will be mainly described below.

A storing section 14 in an acceptance apparatus 10 in the medical image classification system 100' stores a position information table illustrated in FIG. 14. The position information table is a table to which a medical image classification apparatus 30 refers before a patient returns a beacon B.

First, a medical clerk accepts a patient and lends a beacon B to the patient. Then, the medical clerk inputs, into the acceptance apparatus 10, the patient ID of the accepted patient, the beacon ID of the lent beacon B, the lending time of the beacon B, and the position information of a location where an examination is intended to be carried out. The acceptance apparatus 10 accepts the inputs and generates a position information table.

The position information of a location where an examination is intended to be carried out, which is information indicating a patient's destination, is, for example, the number of an examination room (Room 001 in the example of FIG. 14). The association relationship between the number of the examination room and longitude/latitude information is stored in advance in the acceptance apparatus 10. The number of the examination room and the longitude/latitude information are associated with each other as accompanying information when the number of the examination room is accepted (longitude x1, latitude y1, and the like in the example of FIG. 14).

The medical image classification apparatus 30 in the medical image classification system 100' receives a beacon ID and current position information (longitude/latitude information), transmitted by a beacon B having a GPS function, via a communicator 37. A patient correction/incorrection determination process, carried out by the medical image classification apparatus 30, for determining whether or not a patient is at an examination location where the patient should be examined will be described with reference to FIG. 15.

In the patient correction/incorrection determination process of this FIG. 15, it is monitored whether or not a controller 31 in the medical image classification apparatus 30 receives the beacon ID and the current position information from the beacon B via the communicator 37 (step S41; No). It is assumed that the controller 31 receives the beacon ID and the current position information transmitted from the beacon B carried by the patient before a doctor starts the examination of the patient (step S41; Yes). Then, the processes of step S42 or later are carried out.

First, an acquiring section 32 acquires the position information table. Specifically, the acquiring section 32 acquires the position information table from the acceptance apparatus 10 via the communicator 37. Then, the controller 31 specifies the patient ID of a patient examined by a doctor and the position information of a location where an examination is intended to be carried out (information indicating the destination of the patient) with reference to the position information table (step S43).

Specifically, the controller 31 specifies the patient ID and the position information of the location where the examination is intended to be carried out from the position information table based on the beacon ID received in step S41 and on a current time specified by a timer and/or the like. For example, when a beacon ID of 1 is received from a beacon 1 and the current time is 9:10, the controller 31 refers to the position information table, a patient ID of A and Room 001 (longitude x1 and latitude y1) which correspond with the beacon ID of 1 and a lending time of 9:00 followed by the current time of 9:10 are specified.

Then, the controller 31 determines whether or not the specified position information of the location where the examination is intended to be carried out and the received current position information correspond with each other (step S44). Specifically, the controller 31 determines whether or not the position information (longitude/latitude information) indicating the patient's destination and the current position information (longitude/latitude information) of the patient correspond with each other.

For example, the controller 31 determines whether or not the longitude x1 and latitude y1 of Room 001 which are the items of position information of the location where the examination is intended to be carried out and the current position information (longitude/latitude information) received from the beacon 1 correspond with each other. In this case, because it is not necessary that the longitude and the latitude accurately correspond with each other but it is necessary only that it can be determined whether or not the patient is in an examination room in which the patient should be examined, the errors of the longitude and the latitude are preferably set in accordance with the size of the interior of the examination room. For example, in step S44, it may be determined whether or not the specified position information of the location where the examination is intended to be carried out and the received current position information are within predetermined errors.

When both correspond with each other (step S44; Yes), for example, when the position information of the location where the examination is intended to be carried out and the current position information correspond with each other at the longitude x1 and the latitude y1, the patient A with the patient ID of A is in Room 001 which is the location where the examination is intended to be carried out, and the process is therefore ended without providing an error notification.

Alternatively, when the position information of the location where the examination is intended to be carried out and the current position information do not correspond with each other (step S44; No), the patient is not in the location where the examination is intended to be carried out (in the case of the example described above, the patient A with the patient ID of A is not in Room 001 at the location where the examination is intended to be carried out), and an error notification is therefore provided (step S45) to end the process. The error notification is, for example, a voice notification for notifying a doctor that a patient is not a patient intended to be examined or a voice notification for providing a notification that a patient is at a location different from a location where an examination is intended to be carried out. In the correction/incorrection determination process, the acquiring section 32 corresponds to a position information receiver, and the controller 31 corresponds to a specifier and a notifier.

In such a manner, in the medical image classification system 100' according to the alternative example, the current position information of a patient is specified from a beacon B having a GPS function, and it is determined whether or not the specified current position information corresponds with information indicating a patient's destination in a position information table (position information of a location where an examination is intended to be carried out). Thus, it can be determined whether or not the patient is at an examination location where the patient should be examined. Accordingly, a doctor can find, before examining the patient, whether or not the patient is a patient whom the doctor intends to take charge of examining, and the patient can find, before the examination, whether or not the patient is in an incorrect examination room.

In the present alternative example, the position information table is used, without limitation thereto. For example, a patient specification table may be used instead of the position information table. Specifically, in the patient specification table, a usage time period in which a beacon B is used may be used in place of a lending time in which the beacon is lent until the beacon B is returned, and one column may be added for the position information of a location where an examination is intended to be carried out. As a result, the patient specification table can be used not only for classification but also for correction/incorrection determination.

In the alternative example described above, the medical image classification apparatus 30 carries out the correction/incorrection determination process, without limitation thereto. The medical image acquisition apparatus 20 may carry out the correction/incorrection determination process as long as the medical image acquisition apparatus 20 can acquire the position information table from the acceptance apparatus 10 by wired communication or wireless communication. In this case, the medical image acquisition apparatus 20 preferably allows an error message to be displayed as an error notification on a display 25.

The example embodiment and alternative example are described above based on the premise that a medical image is a dermoscopy image, without limitation thereto. It is essential only that such an image is a medical image. Therefore, for example, roentgen images, X-ray images, computed tomography (CT) images, magnetic resonance imaging (MRI) images, and the like are also acceptable.

The medical image classification systems 100 and 100' are described based on the premise that the medical image classification systems 100 and 100' are applied to medical settings. It is parenthetically remarked that in this case, users of the beacon B are patients, users of the medical image acquisition apparatus 20 and the medical image classification apparatus 30 are doctors, and objects to be classified are medical images, without limitation thereto. For example, images may be classified per subject based on the premise that users of the beacon B are subjects, users of the medical image acquisition apparatus 20 and the medical image classification apparatus 30 are photographers, and objects to be classified are the images showing the subjects (for example, landscape images and/or the like).

Each function of the acceptance apparatus 10, medical image acquisition apparatus 20, and medical image classification apparatus 30 of the present disclosure can also be carried out by a computer such as a usual PC.

Specifically, the example embodiment is described above based on the premise that the program for each process (acceptance process, imaging process, and classification process) carried out by each apparatus is stored in advance in the ROMs of the controllers 11, 21, and 31 of each apparatus. However, a computer capable of implementing the above-described function of each component may also be configured by distributing the program for each process stored in a non-transitory computer-readable recording medium such as a flexible disc, a compact disc read only memory (CD-ROM), a digital versatile disc (DVD), or a magneto-optical disc (MO) and by installing the program on the computer. For example, the program stored in a disk device and/or the like included in a server device on a communication network such as the Internet may also be downloaded to a computer.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A medical image classification system comprising:
an acceptance apparatus,
a medical image acquisition apparatus, and
a medical image classification apparatus,
wherein the acceptance apparatus comprises:
a first processor that is configured to accept an input of patient identification information for identifying a patient and medium identification information of a portable information retaining medium carried by the patient; and
a first memory that stores first association information in which the accepted patient identification information and the accepted medium identification information are associated with each other;

wherein the medical image acquisition apparatus comprises:
  a second processor that is configured to:
    acquire the medium identification information from the portable information retaining medium carried by the patient; and
    acquire, via an imaging device including an image sensor, a medical image for diagnosing the patient; and
  a second memory that stores second association information in which medical image identification information for identifying the acquired medical image and the acquired medium identification information are associated with each other;
wherein the medical image classification apparatus comprises:
  a third processor that is configured to:
    acquire the first association information stored by the first memory;
    acquire the second association information stored by the second memory; and
    perform classification of the medical image identification information per the patient identification information based on the medium identification information in the first association information and the second association information; and
  wherein:
    the first memory further stores a usage time period in which the patient carrying the portable information retaining medium uses the portable information retaining medium, associated with the patient identification information and the medium identification information, as the first association information;
    the second memory further stores a photographing time at which the medical image is photographed, associated with the medical image identification information and the medium identification information, as the second association information;
    the third processor of the medical image classification apparatus, in performing the classification, is further configured to:
      perform a first determination to determine whether or not the medium identification information in the second association information and the medium identification information in the first association information correspond with each other; and
      perform a second determination to determine whether or not the photographing time in the second association information is within the usage time period in the first association information; and
    the classification is performed based on a determination result from the first determination and the second determination.

2. The medical image classification system according to claim 1, wherein:
  the third processor of the medical image classification apparatus assigns the medical image identification information to the patient identification information and performs the classification when the third processor determines in the first determination that the medium identification information in the second association information and the medium identification information in the first association information correspond with each other, and determines in the second determination that the photographing time is within the usage time period.

3. The medical image classification system according to claim 1, wherein:
  the portable information retaining medium is a portable transmission medium; and
  the medical image acquisition apparatus comprises a receiver that receives the medium identification information, which is transmitted by the portable transmission medium, and the second processor of the medical image acquisition apparatus acquires the medium identification information via the receiver.

4. The medical image classification system according to claim 3, wherein:
  the first memory further stores position information on a location at which a patient carrying the portable transmission medium intends to see a doctor, associated with the patient identification information and the medium identification information, as the first association information;
  the medical image classification apparatus further comprises a position information receiver that receives the medium identification information of the portable transmission medium, transmitted from the portable transmission medium carried by the patient, and current position information indicating a current position of the portable transmission medium;
  the third processor of the medical image classification apparatus is further configured to:
    specify the position information on the location at which the patient intends to see the doctor from the first association information based on the medium identification information received by the position information receiver; and
    provide a notification that the patient is not at the location at which the patient intends to see the doctor when the position information on the location at which the patient intends to see the doctor, specified by the third processor, and the current position information received by the position information receiver do not correspond with each other.

5. The medical image classification system according to claim 3, wherein the portable transmission medium is a beacon in accordance with Bluetooth (registered trademark) Low Energy or a contactless IC card in accordance with Near Field Communication (NFC).

6. The medical image classification system according to claim 1, wherein the medical image is a dermoscopy image of a patient, photographed through a dermoscope.

7. The medical image classification system according to claim 1, wherein the second memory is a non-transitory transportable storage medium.

8. A medical image classification method for a medical image classification apparatus comprising a processor, the method comprising, with the processor:
  acquiring a patient specification table that stores patient identification information for identifying a patient, medium identification information of a portable information retaining medium carried by the patient, and a usage time period of the portable information retaining medium associated with one another;
  acquiring an image specification table in which image identification information of a medical image photographing an affected area of the patient, the medium identification information, and a photographing time when the affected area is photographed are associated with one another;

selecting an item of medium identification information from among the medium identification information in the image specification table;

determining whether the patient specification table includes an item of medium identification information that matches the selected item of medium identification information;

determining, when the patient specification table includes the item of medium identification information that matches the selected item of medium identification information in the image specification table, whether the photographing time is within the usage time period; and classifying the medical image by assigning, when the photographing time is within the usage time period, an image ID of the image specification table to the patient identification information of the patient specification table.

9. A medical image classification system comprising:
an acceptance apparatus,
a medical image acquisition apparatus, and
a medical image classification apparatus,
wherein the acceptance apparatus comprises:
 a first processor that is configured to accept an input of patient identification information for identifying a patient and medium identification information of a portable information retaining medium carried by the patient; and
 a first memory that stores first association information in which the accepted patient identification information and the accepted medium identification information are associated with each other;
wherein the medical image acquisition apparatus comprises:
 a second processor that is configured to:
  acquire the medium identification information from the portable information retaining medium carried by the patient; and
  acquire, via an imaging device including an image sensor, a medical image for diagnosing the patient; and
 a second memory that stores second association information in which medical image identification information for identifying the acquired medical image and the acquired medium identification information are associated with each other;
wherein the medical image classification apparatus comprises:
 a third processor that is configured to:
  acquire the first association information stored by the first memory;
  acquire the second association information stored by the second memory; and
  perform classification of the medical image identification information per the patient identification information based on the medium identification information in the first association information and the second association information; and
wherein:
 the portable information retaining medium is a portable transmission medium;
 the medical image acquisition apparatus comprises a receiver that receives medium identification information transmitted by the portable transmission medium, and the second processor of the medical image acquisition apparatus acquires the medium identification information via the receiver;
 the second processor of the medical image acquisition apparatus is further configured to select medium identification information with maximum reception strength when the receiver receives a plurality of items of medium identification information; and
 the second memory stores the second association information in which the medium identification information selected by the second processor and the medical image identification information are associated with each other.

* * * * *